United States Patent
Davidson et al.

(10) Patent No.: US 10,434,218 B2
(45) Date of Patent: *Oct. 8, 2019

(54) PRE-STRESSING AND CAPPING BIOPROSTHETIC TISSUE

(71) Applicant: Edwards Lifesciences Corporation, Irvine, CA (US)

(72) Inventors: James A. Davidson, San Juan Capistrano, CA (US); Jeffrey S. Dove, Santa Ana, CA (US); Darin P. Dobler, Aliso Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,339

(22) Filed: Jan. 24, 2018

(65) Prior Publication Data

US 2018/0147323 A1 May 31, 2018

Related U.S. Application Data

(63) Continuation of application No. 14/797,449, filed on Jul. 13, 2015, now Pat. No. 9,878,068, which is a continuation of application No. 12/135,507, filed on Jun. 9, 2008, now Pat. No. 9,101,691.

(60) Provisional application No. 60/943,118, filed on Jun. 11, 2007.

(51) Int. Cl.
| | |
|---|---|
| *A61L 27/00* | (2006.01) |
| *A61L 27/36* | (2006.01) |
| *A61F 2/24* | (2006.01) |
| *A61L 27/50* | (2006.01) |

(52) U.S. Cl.
CPC ........ *A61L 27/3625* (2013.01); *A61F 2/2412* (2013.01); *A61L 27/3683* (2013.01); *A61L 27/3687* (2013.01); *A61L 27/3691* (2013.01); *A61L 27/507* (2013.01); *A61F 2210/0004* (2013.01); *A61F 2210/0076* (2013.01); *A61L 2400/02* (2013.01); *A61L 2430/20* (2013.01); *A61L 2430/40* (2013.01)

(58) Field of Classification Search
CPC ............ A61L 27/3625; A61L 27/3683; A61L 27/3687; A61L 27/3691; A61L 27/507; A61L 2400/02; A61L 2430/20; A61L 2430/40; A61F 2/2412; A61F 2210/0004; A61F 2210/0076; A61F 9/00; A61F 11/00
See application file for complete search history.

(56) References Cited

U.S. PATENT DOCUMENTS

| | | |
|---|---|---|
| 2,393,580 A | 1/1946 | Weiskopf |
| 4,350,492 A | 9/1982 | Wright et al. |
| 4,372,743 A | 2/1983 | Lane |
| 4,624,822 A | 11/1986 | Arru et al. |
| 4,758,151 A | 7/1988 | Arru et al. |
| 4,786,287 A * | 11/1988 | Nashef ................ A61L 27/3687 600/36 |
| 5,116,564 A | 5/1992 | Jansen et al. |
| 5,279,612 A | 1/1994 | Eberhardt |
| 5,329,846 A | 7/1994 | Bonutti |
| 5,397,353 A | 3/1995 | Oliver et al. |
| 5,460,962 A | 10/1995 | Kemp |
| 5,476,516 A | 12/1995 | Seifter et al. |
| 5,695,820 A | 12/1997 | Davis et al. |
| 5,713,953 A | 2/1998 | Vallana et al. |
| 5,720,894 A | 2/1998 | Neev et al. |
| 5,919,472 A | 7/1999 | Trescony et al. |
| 5,921,980 A | 7/1999 | Kim |
| 5,945,319 A | 8/1999 | Keogh |
| 5,993,844 A | 11/1999 | Abraham et al. |

(Continued)

FOREIGN PATENT DOCUMENTS

| | | |
|---|---|---|
| EP | 0169259 A1 | 1/1986 |
| EP | 2394673 A1 | 12/2011 |

(Continued)

OTHER PUBLICATIONS

Ogasawara et al. "Reactivity of taurine with aldehydes and its physiological role." Adv Exp Med Biol. 1994;359:71-8. (Year: 1994).*

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona Health Science Center, Tucson, AZ.

(Continued)

*Primary Examiner* — Titilayo Moloye
(74) *Attorney, Agent, or Firm* — Michelle Kim; Darren Franklin; Sheppard, Mullin, Richter & Hampton LLP

(57) ABSTRACT

A treatment for bioprosthetic tissue used in implants or for assembled bioprosthetic heart valves to reduce in vivo calcification is disclosed. The method includes preconditioning, pre-stressing, or pre-damaging fixed bioprosthetic tissue in a manner that mimics the damage associated with post-implant use, while, and/or subsequently applying a calcification mitigant such as a capping agent or a linking agent to the damaged tissue. The capping agent suppresses the formation of binding sites in the tissue that are exposed or generated by the damage process (service stress) and otherwise would, upon implant, attract calcium, phosphate, immunogenic factors, or other precursors to calcification. The linking agent will act as an elastic reinforcement or shock-absorbing spring element in the tissue structure at the site of damage from the pre-stressing. In one method, tissue leaflets in assembled bioprosthetic heart valves are preconditioned by simulating actual flow conditions for a predetermined number of cycles, during or after which the valve is exposed to the capping agent.

13 Claims, 5 Drawing Sheets

(56) References Cited

U.S. PATENT DOCUMENTS

| | | | |
|---|---|---|---|
| 6,017,741 A | 1/2000 | Keogh | |
| 6,132,472 A | 10/2000 | Bonutti | |
| 6,156,030 A | 12/2000 | Neev | |
| 6,165,215 A | 12/2000 | Rottenberg et al. | |
| 6,166,184 A | 12/2000 | Hendriks et al. | |
| 6,174,331 B1 | 1/2001 | Moe et al. | |
| 6,251,579 B1 | 6/2001 | Moore et al. | |
| 6,277,555 B1 | 8/2001 | Duran et al. | |
| 6,293,970 B1 | 9/2001 | Wolfinbarger, Jr. et al. | |
| 6,334,873 B1 | 1/2002 | Lane et al. | |
| 6,352,708 B1 | 3/2002 | Duran et al. | |
| 6,482,199 B1 | 11/2002 | Neev | |
| 6,534,004 B2 | 3/2003 | Chen et al. | |
| 6,582,464 B2 | 6/2003 | Gabbay | |
| 6,589,591 B1 | 7/2003 | Mansouri et al. | |
| 6,605,667 B1 | 8/2003 | Badejo et al. | |
| 6,617,142 B2 | 9/2003 | Keogh et al. | |
| 6,630,001 B2 | 10/2003 | Duran et al. | |
| 6,682,559 B2 | 1/2004 | Myers et al. | |
| 6,872,226 B2 | 3/2005 | Cali et al. | |
| 6,878,168 B2 | 4/2005 | Carpentier et al. | |
| 6,911,043 B2 | 6/2005 | Myers et al. | |
| 7,008,763 B2 | 3/2006 | Cheung | |
| 7,029,434 B2 | 4/2006 | Carpentier et al. | |
| 7,037,333 B2 | 5/2006 | Myers et al. | |
| 7,078,163 B2 | 7/2006 | Torrianni | |
| 7,141,064 B2 | 11/2006 | Scott et al. | |
| 7,143,769 B2 | 12/2006 | Stoltz et al. | |
| 7,214,344 B2 | 5/2007 | Carpentier et al. | |
| 7,238,200 B2 | 7/2007 | Lee et al. | |
| 7,367,969 B2 | 5/2008 | Stoltz et al. | |
| RE40,570 E | 11/2008 | Carpentier et al. | |
| 7,498,565 B2 | 3/2009 | Silberberg et al. | |
| 7,579,381 B2 | 8/2009 | Dove | |
| 7,648,676 B2 | 1/2010 | Mills et al. | |
| 7,682,304 B2 | 3/2010 | Heyninck-Jantz et al. | |
| 7,914,569 B2 | 3/2011 | Nguyen et al. | |
| 7,919,112 B2 | 4/2011 | Pathak et al. | |
| 7,972,376 B1 | 7/2011 | Dove et al. | |
| 8,007,992 B2 | 8/2011 | Tian et al. | |
| 8,043,450 B2 | 10/2011 | Cali et al. | |
| 8,075,615 B2 | 12/2011 | Eberhardt et al. | |
| 8,105,375 B2 | 1/2012 | Navia et al. | |
| 8,136,218 B2 | 3/2012 | Millwee et al. | |
| 8,308,797 B2 | 11/2012 | Paniagua et al. | |
| 8,357,387 B2 | 1/2013 | Dove et al. | |
| 8,361,144 B2 | 1/2013 | Fish et al. | |
| 8,377,143 B2 | 2/2013 | Hamby et al. | |
| 8,475,827 B2 | 7/2013 | Hamby et al. | |
| 2001/0025196 A1 | 9/2001 | Chinn et al. | |
| 2001/0027344 A1 | 10/2001 | Bonutti | |
| 2002/0001834 A1 | 1/2002 | Keogh et al. | |
| 2002/0091441 A1 | 7/2002 | Guzik | |
| 2003/0212454 A1 | 11/2003 | Scott et al. | |
| 2004/0082991 A1* | 4/2004 | Nguyen | A61F 2/2412 623/2.14 |
| 2004/0086543 A1 | 5/2004 | Keogh et al. | |
| 2005/0010773 A1 | 1/2005 | Lapstun et al. | |
| 2005/0119736 A1 | 6/2005 | Zilla et al. | |
| 2005/0136510 A1 | 6/2005 | Hendriks et al. | |
| 2005/0211680 A1 | 9/2005 | Li et al. | |
| 2006/0084957 A1 | 4/2006 | Delfyett et al. | |
| 2006/0099326 A1 | 5/2006 | Keogh et al. | |
| 2006/0110370 A1 | 5/2006 | Pathak et al. | |
| 2006/0193885 A1 | 8/2006 | Leonard Neethling et al. | |
| 2006/0217804 A1 | 9/2006 | Dove | |
| 2006/0217805 A1 | 9/2006 | Dove | |
| 2007/0050014 A1 | 3/2007 | Johnson | |
| 2007/0073392 A1 | 3/2007 | Heyninck-Jantz et al. | |
| 2007/0203576 A1 | 8/2007 | Lee et al. | |
| 2007/0254005 A1 | 11/2007 | Pathak et al. | |
| 2007/0292459 A1 | 12/2007 | Cooper et al. | |
| 2008/0302372 A1 | 12/2008 | Davidson et al. | |
| 2008/0319166 A1 | 12/2008 | Shen | |
| 2009/0130162 A2 | 5/2009 | Pathak et al. | |
| 2009/0137999 A1 | 5/2009 | Silberberg et al. | |
| 2009/0188900 A1 | 7/2009 | Cali et al. | |
| 2009/0326524 A1 | 12/2009 | Cali et al. | |
| 2010/0036484 A1 | 2/2010 | Hariton et al. | |
| 2011/0092966 A1 | 4/2011 | Guo et al. | |
| 2011/0177150 A1 | 7/2011 | Pathak et al. | |
| 2011/0214398 A1 | 9/2011 | Liburd et al. | |
| 2011/0238167 A1 | 9/2011 | Dove et al. | |
| 2011/0295363 A1 | 12/2011 | Girard et al. | |
| 2011/0300625 A1 | 12/2011 | Paniagua et al. | |
| 2011/0306124 A1 | 12/2011 | Strasly et al. | |
| 2011/0311493 A1 | 12/2011 | Dove et al. | |
| 2012/0035720 A1 | 2/2012 | Cali et al. | |
| 2012/0059487 A1 | 3/2012 | Cunanan et al. | |
| 2012/0067855 A1 | 3/2012 | Guo et al. | |
| 2012/0078356 A1 | 3/2012 | Fish et al. | |
| 2012/0095551 A1 | 4/2012 | Navia et al. | |
| 2012/0123557 A1 | 5/2012 | Carpentier et al. | |
| 2012/0185038 A1 | 7/2012 | Fish et al. | |
| 2012/0328905 A1 | 12/2012 | Guo et al. | |
| 2013/0122583 A1 | 5/2013 | Neethling | |
| 2013/0238088 A1 | 9/2013 | Navia et al. | |

FOREIGN PATENT DOCUMENTS

| | | |
|---|---|---|
| WO | 8404894 A1 | 12/1984 |
| WO | 9511047 A1 | 4/1995 |
| WO | 9522361 A1 | 8/1995 |
| WO | 9534332 A1 | 12/1995 |
| WO | 9613227 A1 | 5/1996 |
| WO | 9807452 A1 | 2/1998 |
| WO | 9843556 A1 | 10/1998 |
| WO | 0032252 A1 | 6/2000 |
| WO | 2004082536 A1 | 9/2004 |
| WO | 2006026325 A2 | 3/2006 |
| WO | 2006099334 A2 | 9/2006 |
| WO | 2013009851 A2 | 1/2013 |

OTHER PUBLICATIONS

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Grabenwoger, M. et al. "Decreased Tissue Reaction to Bioprosthetic Heart Valve Material after L-glutaimc acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium-Binding Amino Acid, y-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

Neethling, W, et al. Enhanced Biostability and Biocompatibility of Decellularized Bovine Pericardium, Crosslinked with an Ultra-Low Concentration Monomeric Aldehyde and Treated with ADAPT®, J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

(56) References Cited

OTHER PUBLICATIONS

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12 (1):93-100.

Sabbah, Hani, Mechanical STresses on Closed Cusps of Porcine Bioprosthetic Valves, The Annuals of Thoracic Surgery, 42,93-96, 1986.

Zilla, Peter, Carbodiimide Treatment Dramatically Potentiates the Anticalcific Effect of Alpha-Amino Oleic Acid on Glutaraldehyde-Fixed Aortic Wall Tissue, Ann Torac Surg, 79, 905-10, 2005.

* cited by examiner

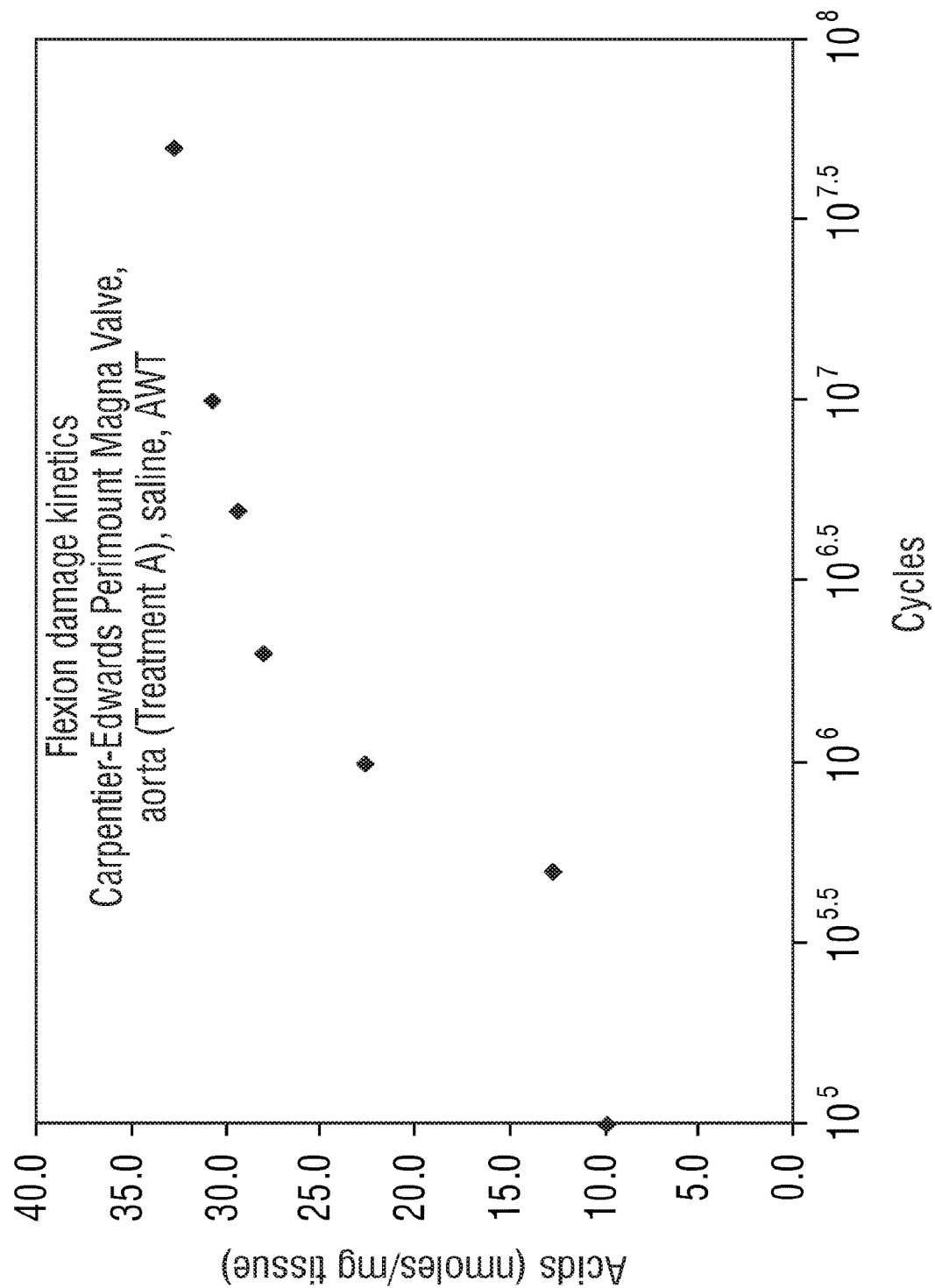

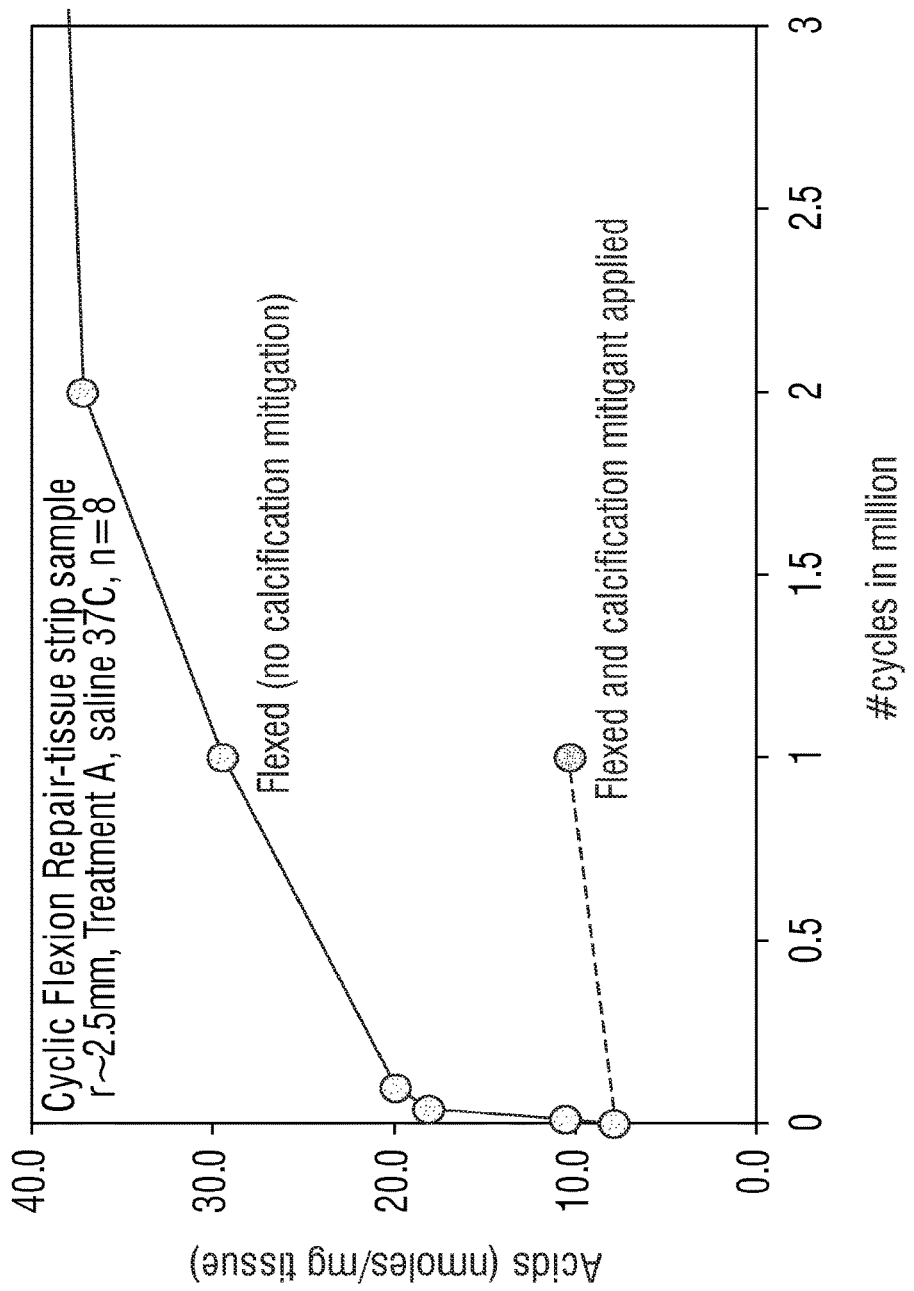

PRE-STRESSING AND CAPPING BIOPROSTHETIC TISSUE

CROSS REFERENCE TO RELATED APPLICATIONS

This application is a continuation of U.S. application Ser. No. 14/797,449, filed Jul. 13, 2015, now U.S. Pat. No. 9,878,068, which is a continuation of U.S. application Ser. No. 12/135,507, filed Jun. 9, 2008, now U.S. Pat. No. 9,101,691, which claims the benefit of U.S. Application No. 60/943,118, filed Jun. 11, 2007, the disclosures all of which are incorporated by reference in their entireties.

BACKGROUND OF THE INVENTION

Heart valve replacement may be indicated when there is a narrowing of the native heart valve, commonly referred to as stenosis, or when the native valve leaks or regurgitates, such as when the leaflets are calcified. In one therapeutic solution, the native valve may be excised and replaced with either a biologic or a mechanical valve.

Tissue-type or "bioprosthetic" valves have flexible leaflets supported by a base structure that project into the flow stream and function much like those of a natural human heart valve by coapting against each other to ensure one-way blood flow. In tissue-type valves, a whole xenograft valve (e.g., porcine) or a plurality of xenograft leaflets (e.g., bovine pericardium) typically provide fluid occluding surfaces. Synthetic leaflets have also been proposed. Two or more flexible leaflets mount within a peripheral support structure, for example as seen in the CARPENTIER-EDWARDS Porcine Heart Valve and PERIMOUNT Pericardial Heart Valve available from Edwards Lifesciences of Irvine, Calif.

Implantable biological tissues can be formed of human tissues preserved by freezing (i.e., cryopreserving) the homograft tissues, or of animal tissues preserved by chemically fixing (i.e., tanning) the xenograft tissues. The type of biological tissues used as bioprostheses include cardiac valves, blood vessels, skin, dura mater, pericardium, small intestinal submucosa ("SIS tissue"), ligaments and tendons. These biological tissues typically contain connective tissue proteins (i.e., collagen and elastin) that act as the supportive framework of the tissue. The pliability or rigidity of each biological tissue is largely determined by the relative amounts of collagen and elastin present within the tissue and/or by the physical structure and configuration of its connective tissue framework. Collagen is the most abundant connective tissue protein present in most tissues. Each collagen molecule is made up of three (3) polypeptide chains intertwined in a coiled helical configuration.

The techniques used for chemical fixation of biological tissues typically involve the exposure of the biological tissue to one or more chemical fixatives (i.e., tanning agents) that form cross-linkages between the polypeptide chains within a given collagen molecule (i.e., intramolecular crosslinkages), or between adjacent collagen molecules (i.e., intermolecular crosslinkages). Examples of chemical fixative agents that have been utilized to cross-link collagenous biological tissues include: formaldehyde, glutaraldehyde, dialdehyde starch, hexamethylene diisocyanate and certain polyepoxy compounds.

One problem associated with the implantation of many bioprosthetic materials is that the connective tissue proteins (i.e., collagen and elastin) within these materials can become calcified following implantation within the body. Such calcification can result in undesirable stiffening or degradation of the bioprosthesis.

Of the various chemical fixatives available, glutaraldehyde (also referred to as simply "glut") has been the most widely used since the discovery of its antiimmunological and antidegenerative effects by Dr. Alain Carpentier in 1968. See Carpentier, A., *J. Thorac. Cardiovascular Surgery*, 58:467-69 (1969). In addition, glutaraldehyde is one of the most efficient sterilization agents. Glutaraldehyde is therefore used as the fixative and the sterilant for many commercially available bioprosthetic products, such as in the bioprosthetic heart valve available from Edwards Lifesciences of Irvine, Calif.

Various techniques have been proposed for mitigating the in vivo calcification of glutaraldehyde-fixed bioprostheses or for otherwise improving the glutaraldehyde fixation process. Included among these are the methods described in U.S. Pat. No. 4,729,139 (Nashef); U.S. Pat. No. 4,885,005 (Nashef et al.); U.S. Pat. No. 4,648,881 (Carpentier et al.); U.S. Pat. No. 5,002,566 (Carpentier); EP 103947 (Pollock et al.), and U.S. Pat. No. 5,215,541 (Nashef et al.). The techniques proposed in U.S. Pat. No. 5,862,806 (Cheung) include dehydration of glutaraldehyde treated tissues prior to the application of a chemical reducing agent such as sodium cyanoborohydride or sodium borohydride. The calcification mitigation techniques found in U.S. Pat. No. 6,471,723 involve addition of a variety of amine functions in an effort to detoxify the aldehyde groups in glutaraldehyde-fixed tissue. These chemicals are not permanently attached to the tissue and will diffuse out of the tissue over time. The use of reducing agents in conjunction with ethanol treatment is shown in Connolly, J., *J. Heart Valve Disease*, 13:487-493 (2004) as being beneficial for mitigating calcification. This publication indicates that the use of reducing agents does not adversely affect the morphology or tissue shrinkage temperature of the tissue.

Recently a new technique of calcium mitigation by elevated temperature fixation of the tissue in glutaraldehyde has been developed and was described in U.S. Pat. No. 6,561,970 (Carpentier et al.), and in combination with relative tissue/fluid movement in U.S. Pat. No. 5,931,969 (Carpentier et al.). Another technique involving adjusting the pH of a glutaraldehyde fixation solution is disclosed in U.S. Pat. No. 6,878,168 (Carpentier et al.). A commercial embodiment, the Edwards Lifesciences XenoLogiX™ Tissue Treatment, eliminates up to 98% of phospholipids in an attempt to reduce calcium binding sites. In the Carpentier-Edwards ThermaFix™ Advanced Heart Valve Tissue Process also from Edwards Lifesciences, both thermal and chemical treatments are used to remove unstable glutaraldehyde molecules which reduces calcium binding sites, resulting in a marked reduction in calcium uptake versus glutaraldehyde-only controls.

Although some of these known techniques have proven to be somewhat effective, there remains a need for further improvements to lessen the propensity for long-term post-implantation calcification of fixed bioprosthetic tissues for use in implants, in particular heart valves. The prior art does not address the changes within the tissue that can occur as a result of the service (implant) environment.

SUMMARY OF THE INVENTION

The present invention accounts for certain detrimental changes within the tissue that can occur as a result of the service (implant) environment. Namely, when the tissue is cyclically stressed during normal service, certain potential binding sites for calcification, immune system attack, etc. are created. The present invention involves pre-stressing the tissue to expose such binding sites, and then capping or otherwise neutralizing such sites.

A method of treating bioprosthetic implant tissue to reduce in vivo calcification of the present invention comprises at least partially cross-linking bioprosthetic implant tissue, then stressing the cross-linked tissue; and applying a calcification mitigant to the stressed, cross-linked tissue. The calcification mitigant may be a capping agent solution having at least one constituent that can bind to calcium, phosphate, or immunogenic factor binding sites. Alternatively, the calcification mitigant is a linking agent solution including a long elastic molecule.

If the calcification mitigant comprises a capping agent, it is desirably selected from the group consisting of: an amine, an amino acid, an amino sulfonate, a hydrophilic multifunctional polymer, a hydrophobic multifunctional polymer, α-dicarbonyl, a hydrazides, a N,N-disuccinimidyl carbonate, a carbodiimide, 2-chloro-1-methylpyridinium iodide (CMPI), an antibiotic, a cell recruiting agent, a hemocompatibility agent, an antiinflamatory agent, an antiproliferative agent, an immunogenic suppressing agent, a reducing agent, and a mono-, di- or polyepoxy alkane.

The calcification mitigant is desirably delivered in one or a combination of the following solutions: an aqueous solution such as an aqueous buffered solution, water, alcohols, glycerol, or plasticizers, an organic solvent, and an organic buffered solution.

The tissue is preferably fully cross-linked prior to stressing. In one embodiment, the tissue comprises precut heart valve leaflets mounted and flexed in a suitable flow apparatus. Alternatively, the tissue may be bulk sheets of tissue flexed in a suitable apparatus. Still further, the bioprosthetic implant tissue may be a bioprosthetic heart valve, and the step of stressing comprises subjecting the heart valve to pulsed fluid flow therethrough. Desirably, the heart valve is subjected to pulsed fluid flow for at least 100 cycles.

In a preferred embodiment, the step of stressing comprises subjecting the bioprosthetic implant tissue to a simulated post-implant physiological environment. Additionally, the step of stressing comprises subjecting the bioprosthetic implant tissue to at least one stress-accelerating environmental parameter. For instance, the stress-accelerating environmental parameter may comprise a rapid pulsed fluid flow in a range of 4-1500 Hz, an elevated temperature range of 26-65° C., an acidic solution of pH of 4-7, an alkaline solution of pH 8-10, an oxidizing solution, or at least two of the preceding.

Preferably, the step of stressing is done until the newly exposed sites to be capped on the bioprosthetic tissue increase by at least 10%. Another measure is to stress the tissue until the level of damage in the bioprosthetic implant tissue increases by about 10%. Alternatively, the stressing is done at least until the rate of acid production in the bioprosthetic implant tissue decreases by about 10%.

The steps of first stressing the tissue and then applying a calcification mitigant thereto may be done multiple times. In addition, the steps of first stressing the tissue and then applying a calcification mitigant thereto may be done at least twice with different calcification mitigants.

Another aspect of the invention is a method of treating bioprosthetic implant tissue to reduce in vivo calcification, comprising cyclically stressing the bioprosthetic implant tissue until the rate of acid production in the bioprosthetic implant tissue decreases by about 10%, and then applying a calcification mitigant to the stressed tissue. Desirably, the bioprosthetic implant tissue comprises a bioprosthetic heart valve, and the step of stressing comprises subjecting the heart valve to pulsed fluid flow therethrough. The step of stressing may be done until the rate of increase of the acid level of the bioprosthetic implant tissue levels off. The calcification mitigant may be a capping agent solution having at least one constituent that can bind to calcium or phosphate, and/or immunogenic binding sites. Alternatively, the calcification mitigant comprises a linking agent solution including a long elastic molecule.

Another aspect of the invention is method of treating a bioprosthetic heart valve to reduce in vivo calcification, comprising mounting a bioprosthetic heart valve in a simulated fluid flow system, subjecting the bioprosthetic heart valve to pulsed fluid flow for at least 100 cycles, then applying a calcification mitigant to the bioprosthetic heart valve. Desirably, the bioprosthetic heart valve is subjected to pulsed fluid flow for at least 100,000 cycles. The steps of first subjecting the bioprosthetic heart valve to pulsed fluid flow and then applying a calcification mitigant thereto may be done multiple times. The steps of first subjecting the bioprosthetic heart valve to pulsed fluid flow and then applying a calcification mitigant thereto may be done at least twice with different calcification mitigants. Preferably, the step of subjecting is done until the rate of increase of the acid level of the bioprosthetic implant tissue levels off. The calcification mitigant may be a capping agent solution having at least one constituent that can bind to calcium or phosphate, and/or immunogenic binding sites. Alternatively, the calcification mitigant comprises a linking agent solution including a long elastic molecule.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIG. 6 is a graph showing the level of acid generation with increasing cycles from a whole prosthetic heart valve in an accelerated wear tester (AWT); and FIG. 7 is a graph showing how the present calcification mitigation process greatly reduces the acid levels in a tissue strip subjected to flexion cycles.

DESCRIPTION OF THE PREFERRED EMBODIMENTS

Figure 1:
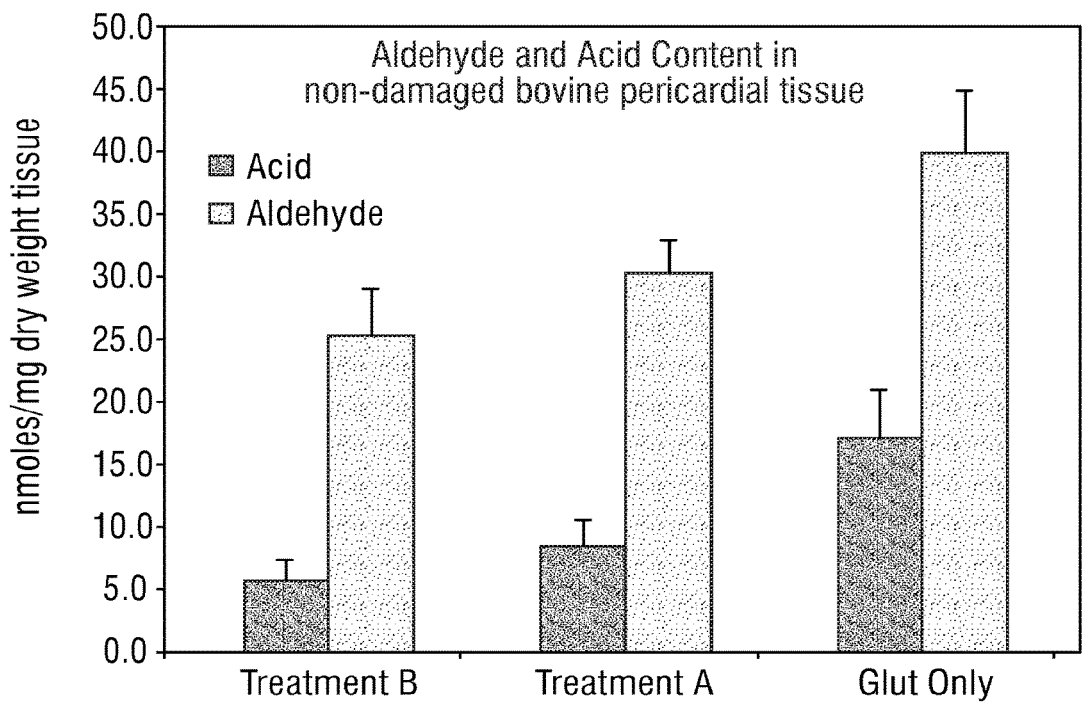
FIG. 1 is a graph showing the aldehyde and acid content in bovine pericardial tissue after several different chemical treatments.

Unlike the prior art that focuses only on "as-processed tissue" and without any consideration of how the tissue calcification propensity can change from imposed service stresses, the present invention provides an improved bioprosthetic tissue treatment process that is believed to greatly reduce the potential for calcification after implantation. "Bioprosthetic tissue" in this sense means at least bovine pericardium and whole porcine valves which are commonly used in bioprosthetic heart valves that must endure years and even decades without calcifying. Other tissues that may be improved by the treatment include blood vessels, skin, dura mater, pericardium, small intestinal submucosa ("SIS tissue"), ligaments and tendons. "Implants" in the present application refers not only to heart valves but also to vascular prostheses and grafts, tissue grafts, bone grafts, and orbital implant wraps, among others.

A "bioprosthetic heart valve" in the present application refers to a fully assembled prosthetic valve made at least partly from bioprosthetic tissue. Some whole porcine valves are used in so-called "stentless" bioprosthetic valves in which there is very little if any synthetic material added for support or anchoring purposes. A "stented" bioprosthetic valve typically has some form of synthetic (e.g., polymer or metallic) support for the leaflets, which, as stated, may be the leaflets of a whole porcine xenograft or separate bovine pericardial leaflets.

Prior tissue treatment processes address crosslinking, microbes, and other aspects of the tissue in a "static" setting, and typically involve immersion of the tissue in glutaraldehyde, Tween (polyoxyethylene 20 sorbitan monooleate), ethanol, formaldehyde, and other agents in order to mitigate post-implant calcification. Some prior art processes include the addition of various chemicals either in a static or dynamic (agitation) setting to reduce the toxicity of the crosslinked tissue or mitigate calcification via the use of metal ions (i.e. $Al^{3+}$ or $Fe^{3+}$—see U.S. Pat. No. 5,746,775 Levy) or bulk blocking agents (i.e. 2-amino oleic acid—see U.S. Pat. No. 4,976,733 Giradot). But each of these prior art process methods are only applied to initially processed tissue and not to tissue or tissue devices in a "service setting". The prior art processes are limited to the addition of chemical or biological agents to the crosslinked tissue that are temporarily attached to the tissue, or they are limited to reduction or oxidation of the tissue alone without any addition of "capping agents" (see U.S. Pat. No. 5,862,806 Cheung).

Unlike the various prior art tissue processes, where the goal is to fix (i.e. crosslink, etc.) the tissue, this invention describes an additional process whereby acids and other potential binding sites formed from the fixation processes as well as the "binding sites" and "potential binding sites" that are generated from flexion of fixed tissue and other in vivo service-related, stress-induced damage are "capped". Tissue typically treated with glutaraldehyde, Tween (polyoxyethylene 20 sorbitan monooleate), ethanol, formaldehyde, and other agents can provide useful fixation of the tissue. However, fixation of the tissue will also generate "binding sites" capable of interacting with or attracting calcium, phosphate, immunogenic factors, or other precursors to calcification. For example, there are many negatively charged carboxylic acid groups formed after glutaraldehyde fixation of the tissue and these groups are capable of attracting calcium ions (due to their negative charge and electrostatic interactions with positively charged ions) leading to calcification of the tissue or adverse cellular interactions.

Carboxylic acid groups like that found in glutamic acid or gamma carboxy glutamic acid are known to bind calcium atoms (Hauschka et al., *PNAS* 1975 72:3925). Calcium binding proteins such as bone sialoprotein contain carboxylic acid rich domains designed to attract and bind calcium, leading to hydroxyapatite formation (calcification). The overall level and location of acid groups in these proteins determines the ability of the protein to efficiently bind calcium and form hydroxyapatite (calcification). The term "acid potential" of the tissue refers to the level of these chemical functional groups within the fixed tissue that can or may eventually form acid groups or "binding sites" through any means such as oxidation, dehydration, hydration, or similar processes.

Figure 3:
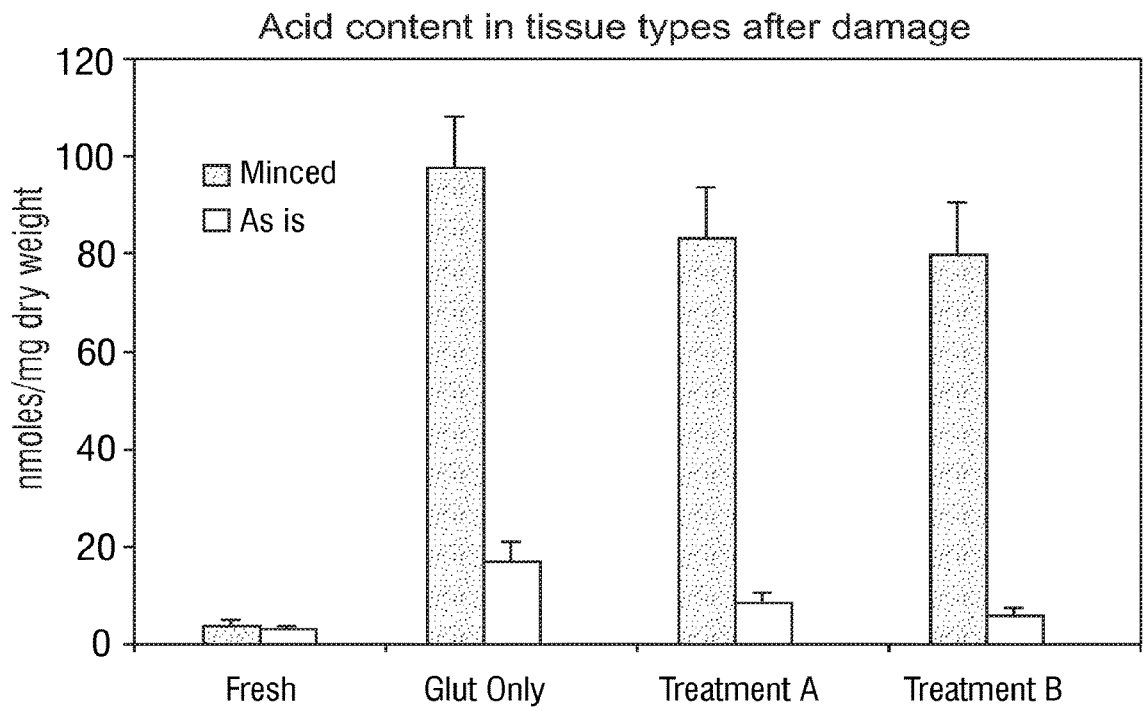
FIG. 3 is a graph illustrating the acid content of glutaraldehyde treated tissue prior to and after being damaged (minced)
Figure 4:
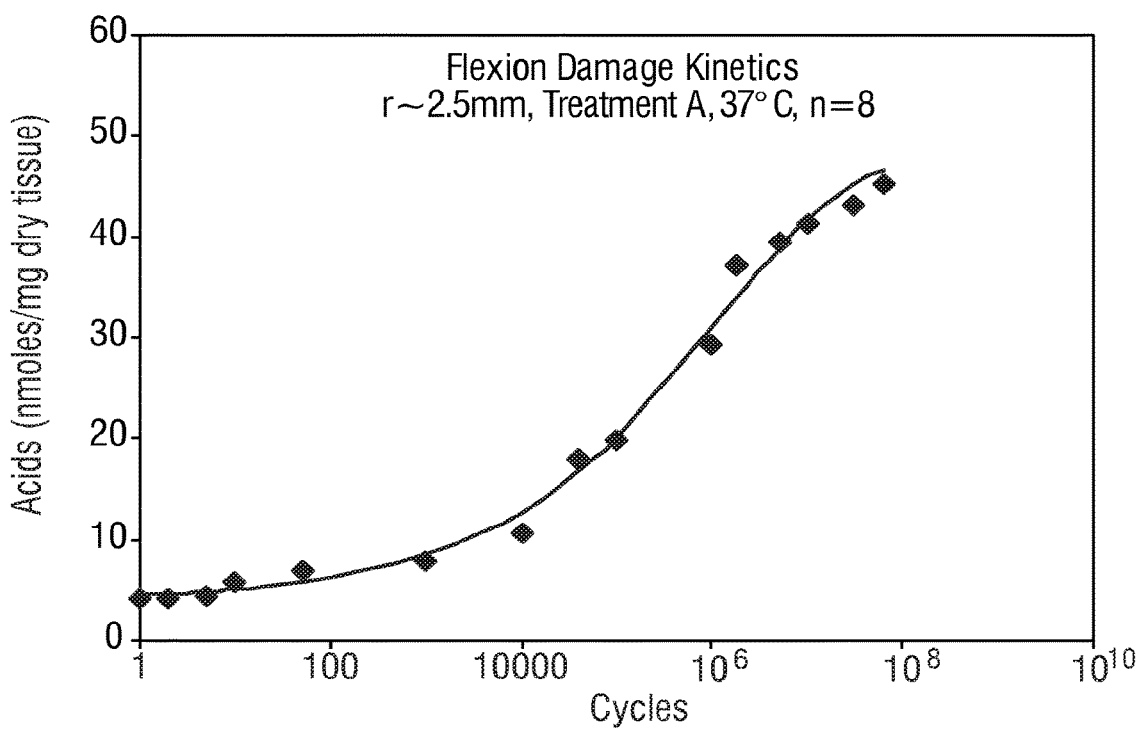
FIG. 4 is a graph showing the acid content of tissue treated in one particular way and subjected to increasing amounts of flexion cycles.

The present invention exploits the fact that subjecting already treated tissue to stress or flexion (micro-fibril damage of the fixed tissue) will generate additional acid binding sites. This is demonstrated by intentionally damaging such tissue, where such damage increases the binding sites dramatically as shown in FIG. 3. Cyclic flexion of glutaraldehyde crosslinked tissue will also increase the level of acids in the tissue compared to static or unflexed tissue (FIG. 4). The flexed or stressed tissue now has a higher "acid potential" and increased propensity for calcification or stimulation of immunogenic responses. The "capping" of both statically formed and stress-induced sites will decrease the overall "acid potential" of the tissue and reduce the risk of calcification and immunogenic response, and is the basic premise of this invention.

The inventors have discovered that bioprosthetic materials, especially tissues used for heart valve leaflets, experience significant post-implant damage which tends to undo some of the beneficial effects of any tissue fixation treatment process. Specifically, after implantation, repeated stress flexion of the tissue leaflets in its in vivo "service"-type environment can create micro-damage to the collagen fibrils and other areas of the leaflets, depending on the severity of the flexion. This progressive leaflet damage process can create new binding sites or potential binding sites that are precursors to calcification and immunogenic related pathways. The present invention describes a method to cap such stress-induced binding sites prior to implantation into the body.

An objective of the invention is the permanent "capping" of the acid groups which would dramatically reduce their ability to attract calcium, phosphate, immunogenic factors, or other groups. This can be accomplished by, for example, capping of acid groups once they are formed or as they are formed through repeated flexion or stress. The term "capping" refers to the blocking, removal, or alteration of some group that would have previously had an adverse effect on the bioprosthesis function. For example, the addition of 1-ethyl-3-[3-dimethylaminopropyl]carbodiimide hydrochloride (EDC), N-hydroxysulfosuccinimide (sulfo-NHS), and ethanolamine will effectively cap the acid groups with a non-reactive alcohol group.

In addition to acid binding sites, tissue treated with glutaraldehyde or other aldehyde containing agents also yields a tissue with many free aldehyde groups, which cause increased toxicity, higher calcification, and creation of immunogenic responses. These aldehyde groups can easily oxidize into carboxylic acid groups (described above) via air oxidation, in vivo blood oxidation, macrophage oxidation, and other similar oxidation pathways. Additionally, as the case for acid binding sites, additional aldehydes can be generated which create more binding sites or acid groups through increased and repeated flexion or stress of the fixed tissue. For example, tissue treated with glutaraldehyde and subsequently stressed or flexed will facilitate the generation of acids from aldehydes as well. Thus, an additional target of the invention includes the permanent capping of aldehyde groups which are potential binding sites in a way that would prevent their ability to transform into acids or other groups and thus further mitigate the potential for calcification in the body (in vivo). In addition to acids and aldehydes there are other possible binding sites such as immunogenic and antigenic factors that are included within the scope of this invention.

The invention's capping process includes the chemical reduction of the tissue which, when applied to the tissue in the presence of a capping agent either prior to, during, or after flexion, will permanently connect the capping agent to the target group. For example, the addition of taurine to the tissue during flexion will cause the taurine group to cap the aldehyde groups as they are formed and the reducing agent, sodium cyanoborohydride, will reduce the temporary Schiff base bond between the aldehyde and the taurine group. The aldehyde group is ultimately replaced with a sulfonate group which may be beneficial for tissue hydration, flexibility, and cell interactions. Another preferred strategy is to cap the acid groups and includes the addition of EDC, sulfo-NHS and ethanolamine. Of course, other capping agents can be used instead of ethanolamine and other reducing agents other than sodium cyanoborohydride are known by those skilled in the art and which are included in the scope of this patent. This new "capped" group will drastically reduce the attraction of calcium, phosphate, immunogenic factors, or other similar agents.

Exemplary capping agents may be selected from the following list amines, including alkyl amines, amino alcohols, ethanolamine; amino acids, including, lysine, hydroxylysine; amino sulfonates, including, taurine, amino sulfates, dextran sulfate, chondroitin sulfate; hydrophilic multifunctional polymers, including polyvinyl alcohol, polyethyleneimine; hydrophobic multifunctional polymers, α-dicarbonyls including methylglyoxal, 3-deoxyglucosone; glyoxal; hydrazides, including adipic; hydrazide, N,N-disuccinimidyl carbonate; carbodiimides, including, 1-ethyl-3-[3-dimethylaminopropyl]carbodiimide hydrochloride (EDC), N-cyclohexyl-N'-(2-morpholinoethyl)carbodiimide (CMC), 1,3-dicyclohexyl carbodiimide (DCC); 2-chloro-1-methylpyridinium iodide (CMPI); an antibiotic; a cell recruiting agent; a hemocompatibility agent, such as heparin; an antiinflamatory agent; an antiproliferative agent; an immunogenic suppressing agent; a reducing agent, including sodium cyanoborohydride, sodium borohydride, sodium bisulfite+acetylacetone, formic acid+formaldehyde; and mono-, di- or polyepoxy alkanes.

By "linking" the binding sites with a long elastic molecule containing at least two or more complimentary reactive functional groups specific for either the newly formed functional groups produced by a stress damage (capping function), or other available nearby functional group, creates a long molecule cross-link that will act as an elastic reinforcement or shock-absorbing spring element in the tissue structure at the site of damage. This will then prevent the cascade failure described above. In the case of adjacent attachment sites, the initial damage (functional group i.e. acid) sites of potential calcification may benefit from being capped in the manner as described for the "capping" of the acid groups, and may be "linked" in concurrent or subsequent treatments. The terms "capping" or "linking" agents all refer to agents for treating pre-stressed tissue to mitigate future potential calcification (i.e., calcification mitigants).

The following table provides various exemplary linking agents, as well as their probable targets and co-reactants, and potential secondary treatments and their co-reactants:

| Polymer/oligomer | Examples | Functional Group X-link Target | Co-reactant(s) | Possible Secondary treatment(s) | Co-reactants |
|---|---|---|---|---|---|
| SYNTHETICS | | | | | |
| Amines | | Aldehydes<br>Acids<br>Alcohols | EDC/S-NHS<br>DSC | Reduction | NaCNBH$_3$ |
| difunctional | Aminopropyl-terminated polytetrahydrofuran | | | | |
| polyfunctional | polyethyleneimine | | | Heparin/reduction | NaCNBH$_3$ |
| Acids | | Amines<br>Alcohols | EDC/S-NHS<br>CMPI | | |
| difunctional | Polyethylene glycol diacid-terminated | | | | |
| polyfunctional | Polyisobutylene-co-maleic acid | | | Capping<br>Sulfonation | Ethanolamine<br>Taurine |
| Alcohols | | Acids<br>Amines | CMPI<br>DSC | | |
| difunctional | Polyurethane-diol terminated | | | | |
| polyfunctional | Polyvinyl alcohol | | | Sulfonation | Triethylamine + sulfur trioxide |
| Oxiranes | | Amines<br>Acids<br>Aldehydes | pH 8<br>NaBF$_4$ | | |
| difunctional | Polyethylene glycol diglycidal ether | | | | |
| polyfunctional | Poly(o-cresyl) glycidyl ether-co-formaldehyde | | | | |
| Silicones | Hydroxyl-terminated polydimethyl siloxane | Acids<br>Amines | CMPI<br>DSC | | |

| Polymer/oligomer | Examples | Functional Group X-link Target | Co-reactant(s) | Possible Secondary treatment(s) | Co-reactants |
|---|---|---|---|---|---|
| NATURAL | | | | | |
| Glycosaminoglycans | Heparin | | | | |
| | Hyaluronic Acid | | | | |
| | Chondroitin Sulfate | | | | |
| Polysaccharides | HetaStarch | | | | |
| | Cellulose | | | | |
| | Dextran | | | | |
| | Chitosan | | | | |
| Proteins | Collagen | | | | |
| | Elastin | | | | |
| | Thrombin | | | | |
| | Laminin | | | | |
| | Connectin | | | | |

Where:

EDC: 1-ethyl-3-[3-dimethylaminopropyl] arbodiimide hydrochloride

SNHS: N-hydroxysulfosuccinamide

DSC: N,N-disuccinimidyl carbonate

CMPI: 2-chloro-1-methylpyridinium iodide $NaBF_4$: sodium tetrafluroborate $NaCNH_3$: sodium cyanoborohydride The effect of preferred capping agents is to not only block functional groups that will attract calcium, phosphate, immunogenic factors, or other similar agents, but to replace those groups with a superior "biological functionality". Biological functionality is defined as the effect of tissue components on the local biology of the implanted material. Improved biological functionality of a tissue treatment may include reduction in overall charge of the tissue, better hemocompatibility, increased tissue hydration, better cell interactions, better flexibility, etc. For example, capping aldehyde functions with taurine would block the aldehyde group from oxidizing into an acid and replace it with a sulfonate group which may be beneficial for tissue hydration, flexibility, and cell interactions. The desired biological functionality of the capped tissue will determine the type of capping compounds employed.

The capping strategy is also designed to block the biological functionality of components of the tissue that may contribute to adverse cellular reactions. Some of these targets include, but are not limited to α-gal, MHC-1 associated proteins, HLA antigens and the like. Thus, the invention is also directed to the capping or blocking of proteins, carbohydrates, lipids, and other components of the tissue that may contribute to cellular reactions. For example, the α-gal carbohydrate may be blocked by treatment with 2-chloro-1-methylpyridinium iodide (CMPI) and other agents that neutralize the hydroxyl groups which are known by those skilled in the art. Another example includes MHC-1 associated proteins that may be capped or effectively neutralized by treatment with EDC and taurine. Also included in the invention capping process is the targeting of proteins, carbohydrates or lipids associated with cell and vessel remnants. For example, fibronectin may be capped or blocked by the addition of methylglyoxal to the tissue. This dicarbonyl is known to bind critical arginine functions within proteins and impairs the biological functionality of these proteins.

In another aspect, the invention provides for automatic capping upon sterilization. For example, the treatment of the tissue with specific capping agents (e.g. glucose and taurine) prior to gamma irradiation sterilization would produce activation of the capping agents upon irradiation. The capping agents added to the tissue would effectively cap targets within the tissue immediately, but sterilization (i.e. with ethylene oxide or gamma irradiation) would generate new binding sites that would then be capped by the residual capping agents within the tissue. Gamma irradiation of collagen is known to cleave peptide bonds within the backbone and produce new functional groups that may have adverse effects on the tissue. These new functional groups are targets or binding sites described in this invention and may be capped or blocked by the capping agents listed herein.

Except for some agitation or pressurization during fixation, the tissue for use in valves and assembled valves of the prior art is not subjected to the amount of stress or damage that occurs after implantation. Indeed, after fixation and valve assembly, the tissues are typically statically immersed in the treatment solutions. In the context of the present invention, "fully fixed bioprosthetic tissue", as mentioned previously, means tissue that has been subjected to at least some cross-linking and/or other treatments to render it stable and durable, essentially ready for implant. Different tissues and different cross-linking treatments require varying time periods to fully fix bioprosthetic tissue, and the duration of the fixation process is therefore, relative. Fixation of bioprosthetic tissue desirably involves treatment with a cross-linking agent, typically glutaraldehyde; or in the case of EDC/SNHS chemistry, hexane diamine and/or suberic acid; or for Denacol (epoxy) chemistry, butanediol diglycidyl ether.

One aspect of the present invention is a process in which fixed bioprosthetic tissue or an assembled valve is preconditioned, pre-stressed, or pre-damaged (where "pre-" refers to pre-implant) and then subjected to a capping agent. Such pre-implant stressing is in addition to the stresses caused by any agitation or pressurization required for fixation.

This, in one embodiment, the methods disclosed herein preempt post-implant damage and subsequent propensity for calcification by pre-stressing the bioprosthetic tissue and then "capping" any new calcification sites. For example, one embodiment of the invention involves damaging ("preconditioning") or stressing a partially fixed bioprosthetic tissue heart valve leaflets and other tissue components (similar to that imposed on the valve post-implantation) prior to implantation, and then suppressing or capping any freshly exposed binding sites that might otherwise initiate calcification. For example, the heart valve leaflets may be repeatedly stressed (e.g., flexed) while immersed in a solution of capping agents that can cap new, freshly exposed calcium or phosphate binding sites (acids, aldehydes, etc.), or sites that can attract antigens and various adverse cell and protein constituents that can initiate an immunologic response (i.e. cell remnants, blood vessel cells, etc.). Alternatively, the heart valve leaflets may be pre-stressed, such as by repeated flexion, and then immersed in the capping agent solution, or some combination of these.

Immunogenic factors are defined as anything causing or involved in stimulating an immunogenic response. This includes any chemical or biological agent capable of inducing an immune type response. For example, vessel and cell membrane components left in the tissue may cause some type of immunogenic or antigenic response from the body's natural immune system. The invention includes capping agents capable of masking, replacing, or blocking these immunogenic elements in the tissue either statically or dynamically. For example, a whole valve could be flexed after fixation and then capped with a non-immunogenic or more hemocompatible capping agent such as heparin. This is different from prior art processes that add heparin to fixed tissue without any flexion of the valve or any consideration of the post-process service conditions. The invention process can be supplemented with a decellularization process to reduce immunologic or antigenic binding sites and potential binding sites and is also within the scope of this invention.

To better understand the principles underlying the treatment techniques of the present invention, a number of graphs in FIGS. 1-5 are presented based on actual testing. As mentioned above, the invention generally comprises treating stressed or damaged (flexed) tissue so that calcium or phosphate binding sites, or other such sites which could trigger calcification, are capped. The correlation between acid binding sites and tissue calcification is compelling (FIG. 2 and Hauschka et al. *PNAS* 1975 72:3925) and it is a well-known fact that acid templating directs mineralization in a variety of species. Thus, an increasing amount of free acids and/or aldehydes in the tissue at the time of implant correlates with the number of such binding sites, and therefore increases the potential for calcification. The amount of free acids and aldehydes present in tissue can be measured by known methods, in particular a standard spectrophotometric assay.

FIG. 1 is a graph showing both the free aldehyde and free acid content in bovine pericardial tissue as measured by the aforementioned technique. It should be understood that all of the tests referred to herein involve glutaraldehyde fixed bovine pericardial tissue. The tissues studied have all been chemically treated, one with glutaraldehyde only, and two others with tissue treatments that have been used by Edwards Lifesciences to prepare commercial bioprosthetic tissue for implant. However, other cross-linking and tissue processing methods can be used and are within the scope of this invention.

The aldehyde and acid content of the tissues is measured subsequent to the chemical treatments, and without any damage or stress imparted to the tissue. On the right side of the graph of FIG. 1, the tissue samples have been treated in glutaraldehyde only, in particular in a solution of 0.625% glutaraldehyde for a period of 14 days. A total of 10 samples were treated and subsequently tested. The measurements showed an average level of about 40 nanomoles of aldehydes and about 17 nanomoles of acids per milligram of dry weight of the tissue.

The middle of the graph of FIG. 1 shows the results from testing a total of 10 tissue samples subjected to Treatment A, which is commercially known as the XenoLogiX™ tissue treatment process from Edwards Lifesciences of Irvine, Calif. Treatment A involves first fixing with glutaraldehyde then treating twice with a sterilant including a cross-linking agent such as formaldehyde, a surfactant such as Tween-80 (polyoxyethylene sorbitan monooleate), and a denaturant such as ethyl alcohol. Both the aldehyde and acid content of the tissue subjected to treatment A were less than glutaraldehyde alone, with the aldehyde content decreasing by about 25% and the acid content by about 50%. This reduction has been attributed to the further reduction of phospholipids which are sources of acid binding sites.

The left side of FIG. 1 shows the results from testing a total of 10 samples subjected to Treatment B, which is commercially known as the Carpentier-Edwards ThermaFix™ tissue treatment process from Edwards Lifesciences. Treatment B is essentially the same as Treatment A, with the addition of a heat treating step after fixing and prior to sterilizing. Both the aldehyde and acid content of the tissue subjected to Treatment B were less than glutaraldehyde alone, with the aldehyde content decreasing by about 33% and the acid content by more than 50%. In addition, Treatment B reduces both the aldehyde and acid content relative to Treatment A by between 10-20%.

Figure 2:
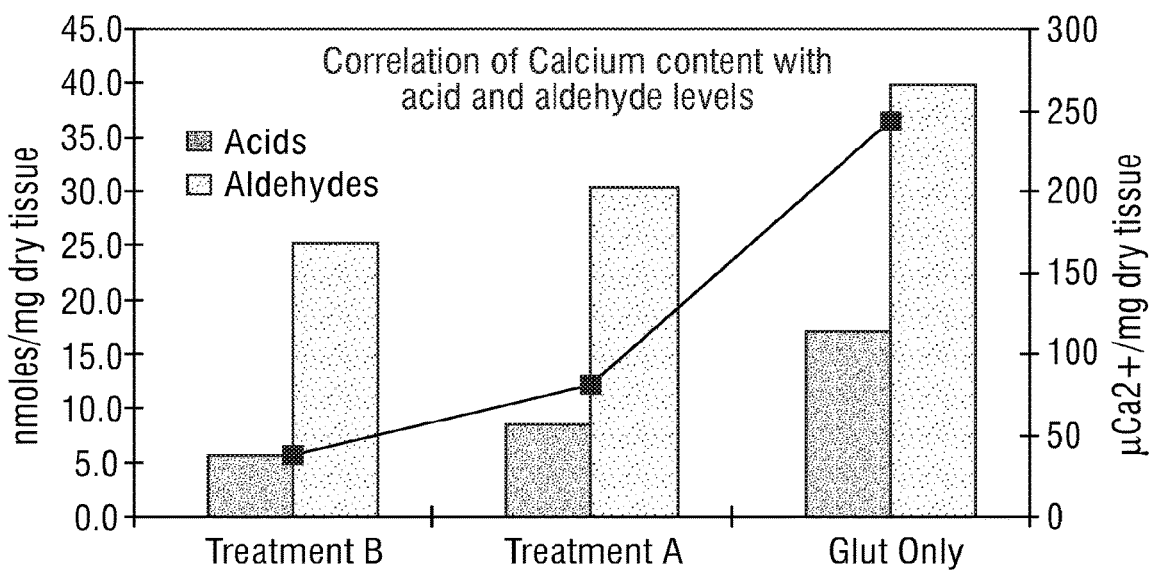
FIG. 2 is a graph correlating the calcium content of in vivo tissue with the corresponding acid and aldehyde content for tissue treated three different ways.

FIG. 2 is a graph that repeats the results of aldehyde/acid content measurements for the three tissue treatments shown in FIG. 1, and also superimposes measurements of calcium uptake from like tissue samples implanted subcutaneously in rabbits from a separate study. These acid levels are measured in the tissue prior to implant and are likely to increase in vivo. FIG. 2 reveals that the amount of calcium found in the implanted tissues essentially correlates with the levels of aldehydes/acids from the three tissue treatments. That is, as the level of free aldehydes and free acids in the various tissue samples decreases, the amount of calcium absorbed upon implant also decreases. Again, it is understood that a number of factors contribute to calcium uptake, but that the availability of certain calcium and phosphate binding sites, among others, is a prime indicator of future calcification. The graph of FIG. 2 therefore suggests that decreasing the levels of aldehydes/acids in the tissue will reduce the propensity for the tissue to calcify.

As mentioned above, it is now understood that postimplant damage or stressing of the bioprosthetic tissue produces a significant increase in the acid and aldehyde calcification binding sites. Evidence of this phenomenon is provided in the graph of FIG. 3. Specifically, as explained above, the level of acids in the tissue correlates directly with the propensity to calcify after implant. FIG. 3 indicates the acid levels in various tissue samples prior to and after damage thereto. The four types of tissue samples are fresh untreated tissue, glutaraldehyde-fixed tissue, and tissue treated with either Treatment A or B. For the damaged condition, the tissue was minced into small pieces. Note that the acid levels in the minced tissue samples greatly exceed that in the non-damaged tissue. Cyclic damage during in vivo service can also generate damage and the production of additional binding sites.

Of course, bioprosthetic tissue used for implants is not subjected to the extreme damage of mincing, nevertheless increased acid levels from increased stress or damage occurs from repeated (cyclic) motion of the leaflets in the service environment. This is shown by FIG. 4 which shows the measured acid content in a number of tissue samples subjected to treatment A after having been subjected to increasing amounts of flexion cycles. Each of the tissue samples was first prepared according to Treatment A. If one assumes a normal average heart rate of 72 beats per minute, the number of cycles per day equals 72×60×24=103,680. At this rate, the final measurement of 7×10$^7$ corresponds to 675 days, or less than two years. FIG. 4 shows, as expected, that increased amount of flexion (micro collagen fibril damage) increases the level of acid binding sites. The acid levels increase fairly rapidly, initially, and then gradually level off. Thus after an initial "wear in" period, the rate of micro damage and associated production of acid binding sites decreased. This effect is analogous to the initial "wear in" period of a car engine.

Figure 5:
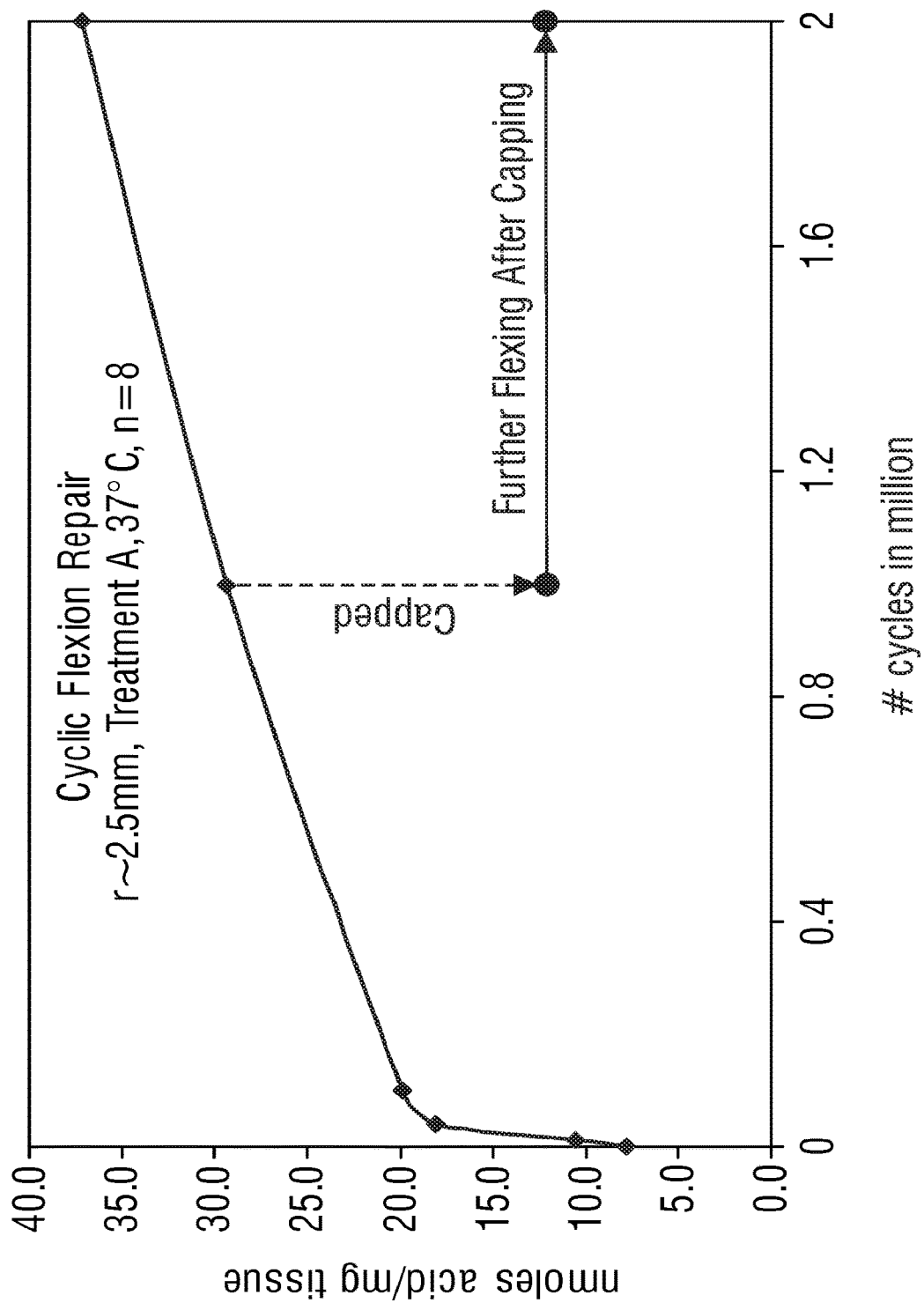
FIG. 5 is a graph showing the acid content of tissue treated in the same way as the tissue in the graph of FIG. 4 and subjected to increasing amounts of flexion cycles, and then after having been treated with a calcification mitigant, in this case a capping agent.

FIG. 5 is a graph showing another representation of the level of charged acid production in tissue as it is cyclicly damaged. Also shown in FIG. 5 is an example of "capping" pre-flexed ("pre-conditioned") tissue after a given amount of flexion cycles (1 million in this case). Importantly, when this pre-conditioned and capped tissue is then flexed further in a similar manner, the production of further acid binding sites is significantly mitigated even after an additional million flex cycles. The acid capping treatment used in this experiment involved a 60 minute incubation of the flexed tissue in 90 mM EDC, 5 mM sulfo-NHS, and 50 mM ethanolamine After the tissue had gone through the acid capping process, the tissue was placed back in the flex tester and flexed an additional 1 million cycles. The tissue strips (n=8) were then removed and the acids were measured.

Based on the foregoing empirical results, the inventors believe that the post-implant damage imparted on bioprosthetic tissue greatly contributes to the propensity for calcification of tissue. In particular, heart valve leaflets are subjected to millions of stress cycles per year, namely flexion of the leaflets during the systole-diastole cycles. This repeated flexion of the tissue leaflets creates localized microdamage to the collagen fibrils and other structures of the tissue leaflets, depending on the severity of the local flexion and other stresses. This progressive leaflet damage process can create new binding sites not previously detected or recognized, as potential attachment sites of calcium and phosphate ions, thereby initiating calcification.

To demonstrate the aforementioned principles on whole prosthetic heart valves, FIG. 6 is a graph showing the level of acid generation with increasing cycles in a heart valve in an accelerated wear tester (AWT). The particular valve tested was the Carpentier-Edwards® Perimount Magna™ Aortic Heart Valve, and the AWT was a standard accelerated wear tester used to validate durability of current products. In a preferred embodiment, a modified wear tester would be used to simulate the cyclic flexion of the implant environment that is simpler than the AWT's presently used for validation. The results indicate the increased amount of flexion (micro collagen fibril damage) increases the level of acid binding sites.

FIG. 7 is a graph showing how the present calcification mitigation process greatly reduces the acid levels in a tissue strip subjected to millions of flexion cycles. Bovine pericardium tissue strips were subjected to simple flexion. At one million cycles, some samples were treated in accordance with the present invention to mitigate the stress damage ("cap" the acid binding sites). In particular, the tissue was treated with an aldehyde capping agent comprising 50 mM taurine and 50 mM borohydride. The difference in subsequently measured acid content between the capped samples and the samples not treated at one million cycles is about 20 nmoles/μg tissue. The inventors believe that this difference in acid levels will greatly reduce the level and speed of post-implant calcification in the capped samples. Likewise, a whole heart valve subjected to the pre-stress and calcification mitigant process described herein will also exhibit a reduction in calcification, and thus an improvement in durability and life.

To help prevent this post-implant damage-calcification process, the present invention involves preconditioning, pre-damaging, or pre-stressing tissue and mitigating by linking or capping the resulting increased calcification initiation sites.

The preferred embodiments include, but are not limited to, a whole valve which is placed in an accelerated heart valve simulated service tester or other device to simulate the repeated leaf motion characteristic of that seen by the valve after implantation into the patient (service condition), such as in the following processes:

The fixed tissue valve is cycled in a simulated service environment until the rate of acid binding sites begins to decrease (i.e. about 0.5 to 2 million cycles), and then capped.

The fixed tissue valve is cycled in a simulated service environment until the rate of acid binding sites begins to decrease and while in a solution containing a capping agent.

Embodiments 1 and 2, but where a sterilization step is added during or after the flexion/capping process.

Embodiments 1 and 2, but where the processing is accelerated to reduce overall processing time.

Embodiments 1, 2, 3, 4, and 5 but where the capping agent is for the other newly formed binding sites such as aldehydes or biological-immune related sites.

The aldehyde capping solution may contain an amine (50 mM taurine) and a reducing agent (50 mM sodium borohydride) in 100 mM 3-(N-morpholino)propanesulfonic acid (MOPS) buffer at pH 7.4.

The acid capping solution may contain about 50-200 mM EDC, about 1-10 mM sulfo-NHS, and 10-100 mM ethanolamine.

While the invention has been described in its preferred embodiments, it is to be understood that the words which have been used are words of description and not of limitation. Therefore, changes may be made within the appended claims without departing from the true scope of the invention.

What is claimed is:

1. A bioprosthetic tissue for implantation in a subject, the bioprosthetic tissue comprising:
   a cross-linked bioprosthetic tissue that has been subjected to pulsed fluid flow to produce localized micro collagen fibril damage at sites of flexion and acid binding sites at the sites of flexion; and
   one or more capping agents coupled to the acid binding sites to produce capped acid binding sites prior to implantation into the subject;
   wherein a content of the acid binding sites is at least 10% in the cross-linked bioprosthetic tissue comprising localized micro collagen fibril damage at sites of flexion than in a cross-linked bioprosthetic tissue not having localized micro collagen fibril damage at sites of flexion; and
   wherein the cross-linked bioprosthetic tissue comprising localized micro collagen fibril damage at sites of flexion and capped acid binding sites has a reduced propensity to calcify in vivo as compared to the cross-linked bioprosthetic tissue not having micro collagen fibril damage at sites of flexion and having capped acid binding sites.

2. The bioprosthetic tissue of claim 1, wherein the bioprosthetic tissue is one or a combination selected from the group consisting of: pericardium, porcine valves, blood vessels, skin, dura matter, small intestinal mucosa, ligaments, and tendons.

3. The bioprosthetic tissue of claim 2, wherein the bioprosthetic tissue is a pericardium and the pericardium is a bovine pericardium.

4. The bioprosthetic tissue of claim 1, wherein the bioprosthetic tissue is cross-linked with an aldehyde.

5. The bioprosthetic tissue of claim 4, where in the aldehyde is a glutaraldehyde.

6. The bioprosthetic tissue of claim 1, wherein the one or more capping agents is one or more selected from the group consisting of: an amine, an amino acid, an amino sulfonate, a hydrophilic multifunctional polymer, a hydrophobic multifunctional polymer, an alpha-dicarbonyl, a hydrazide, an N, N-disuccinimidyl carbonate, a carbodiimide, a 2-chloro-1-methylpyridinium iodide (CMPI), an antibiotic, a cell recruiting agent, a hemocompatibility agent, an anti-inflammatory agent, an antiproliferative agent, an immunogenic suppressing agent, a reducing agent, and a mono-, di- or polyepoxy alkane.

7. The bioprosthetic tissue of claim 6, wherein the capping agent is an amine and the amine is an ethanolamine.

8. The bioprosthetic tissue of claim 6, wherein the capping agent is an amino sulfonate and wherein the amino sulfonate is a taurine.

9. An implant comprising the bioprosthetic tissue of claim 1.

10. A bioprosthetic heart valve comprising the bioprosthetic tissue of claim 1.

11. The bioprosthetic tissue of claim 1, wherein the pulsed fluid flow is at least 100 cycles.

12. The bioprosthetic tissue of claim 11, wherein the pulsed fluid flow is at least 100,000 cycles.

13. The bioprosthetic tissue of claim 1, wherein the pulsed fluid flow is in the range of 4 Hz to 1,500 Hz.

* * * * *